United States Patent
Van Haesendonck et al.

(10) Patent No.: US 10,631,547 B2
(45) Date of Patent: Apr. 28, 2020

(54) CAKE BATTERS

(71) Applicant: PURATOS NV, Groot-Bijgaarden (BE)

(72) Inventors: Ingrid Van Haesendonck, Mechelen (BE); Henrik Østdal, Bagsvaerd (DK); Fanny Nguyen, Boninne (BE); Goedele Van Der Biest, Zellik (BE)

(73) Assignee: PURATOS NV, Groot-Bijgaarden (BE)

( * ) Notice: Subject to any disclaimer, the term of this patent is extended or adjusted under 35 U.S.C. 154(b) by 5 days.

(21) Appl. No.: 15/509,513

(22) PCT Filed: Sep. 29, 2015

(86) PCT No.: PCT/EP2015/072381
§ 371 (c)(1),
(2) Date: Mar. 8, 2017

(87) PCT Pub. No.: WO2016/050746
PCT Pub. Date: Apr. 7, 2016

(65) Prior Publication Data
US 2017/0280733 A1 Oct. 5, 2017

(30) Foreign Application Priority Data
Sep. 29, 2014 (BE) .................... 2014/5000

(51) Int. Cl.
| | | |
|---|---|---|
| *A21D 8/04* | (2006.01) | |
| *A21D 10/04* | (2006.01) | |
| *C12N 9/18* | (2006.01) | |
| *C12N 9/26* | (2006.01) | |

(52) U.S. Cl.
CPC ............ *A21D 8/042* (2013.01); *A21D 10/04* (2013.01); *C12N 9/18* (2013.01); *C12N 9/2414* (2013.01); *C12Y 301/01004* (2013.01); *C12Y 301/01032* (2013.01); *C12Y 302/01001* (2013.01); *C12Y 302/01133* (2013.01)

(58) Field of Classification Search
None
See application file for complete search history.

(56) References Cited

U.S. PATENT DOCUMENTS

| | | | | |
|---|---|---|---|---|
| 3,867,556 A | * | 2/1975 | Darragh | A23L 27/80 |
| | | | | 424/493 |
| 8,426,182 B1 | | 4/2013 | Parenicova | |
| 2006/0057270 A1 | * | 3/2006 | Nicolas | A21D 8/042 |
| | | | | 426/549 |
| 2007/0042099 A1 | * | 2/2007 | Stanton | A21D 2/18 |
| | | | | 426/549 |
| 2008/0003341 A1 | * | 1/2008 | Beier | C12N 9/2417 |
| | | | | 426/549 |
| 2008/0009049 A1 | * | 1/2008 | Viksoe-Nielsen | C12P 7/06 |
| | | | | 435/162 |
| 2010/0062105 A1 | * | 3/2010 | Van Haesendonck | A21D 2/261 |
| | | | | 426/18 |
| 2010/0062106 A1 | * | 3/2010 | Mastenbroek | A21D 2/02 |
| | | | | 426/20 |
| 2012/0190072 A1 | * | 7/2012 | Miasnikov | C12Y 301/01004 |
| | | | | 435/72 |
| 2013/0209607 A1 | * | 8/2013 | Rittig | A21D 8/042 |
| | | | | 426/18 |
| 2014/0377407 A1 | | 12/2014 | Parenicova | |
| 2015/0140168 A1 | | 5/2015 | Bellido et al. | |
| 2016/0135472 A1 | * | 5/2016 | Bellido | A21D 8/042 |
| | | | | 426/18 |

FOREIGN PATENT DOCUMENTS

| | | |
|---|---|---|
| EP | 2 486 799 A1 | 8/2012 |
| WO | 2011154529 A1 | 12/2011 |
| WO | 2013160370 A1 | 10/2013 |

OTHER PUBLICATIONS

Chen CN 101347139 Mar. 23, 2011 Derwent Abstract 1 page (Year: 2011).*
PCT International Search Report and Written Opinion dated Jul. 1, 2016 for PCT International Patent Application No. PCT/EP2015/072381, 10 pages.

* cited by examiner

*Primary Examiner* — Felicia C Turner
(74) *Attorney, Agent, or Firm* — Amster, Rothstein & Ebenstein LLP

(57) ABSTRACT

The present invention provides in methods for preparing a cake batter or a cake product prepared from the batter, comprising adding in any order one or more raw starch degrading alpha-amylases and one or more phospholipases to cake batter ingredients, and preparing the cake batter. Also, cake batters or cake products comprising one or more raw starch degrading alpha-amylases and one or more phospholipases are provided herein.

21 Claims, No Drawings
Specification includes a Sequence Listing.

CAKE BATTERS

CROSS-REFERENCE TO RELATED APPLICATIONS

This application is a U.S. national stage entry under 35 U.S.C. § 371 of PCT International Patent Application No. PCT/EP2015/072381, filed Sep. 29, 2015, which claims priority to Belgian Patent Application No. 2014/5000, filed Sep. 29, 2014, the contents of which are incorporated herein by reference in their entirety.

FIELD OF THE INVENTION

The invention relates to new methods to produce cakes with improved texture parameters and mouthfeel.

BACKGROUND OF THE INVENTION

Cakes are batter-based baked products prepared with three major ingredients present in different ratios depending on the type of cake: flour, sugar and eggs (whole eggs and/or egg white and/or egg yolk). Additional ingredients may be for example fats and/or lipids, leavening agents, emulsifiers, milk proteins, hydrocolloids, starch (native, chemically or physically modified), cocoa powder, chocolate, coloring agents, flavors, etc. Cakes may be leavened due to addition of ingredients (ex. baking powder, egg, emulsifier, protein, . . . ) and/or due to the cake preparation process (ex. whipping of the batter). Typical types of cakes are loaf cream and pound cakes, cup cream and pound cakes, sponge cakes, muffins, cake donuts, brownies, etc.

Cake staling is a phenomenon that occurs during storage. Cake staling (also referred as loss of freshness) is a combination of the deterioration of different texture parameters of the cake among which loss of softness, loss of moistness, loss of cohesiveness, increased gumminess and loss of resilience.

The softness of a cake is the feeling related to the force required to compress and bite the cake crumb. Cake moistness is the moist sensation (opposite of dryness) perceived when touching and eating the cake. Touching a moist cake with the lips and/or the hands gives a colder sensation on lips and/or compared to a dry cake. In the mouth a moist cake is felt as humid and juicy. When eating a moist cake, there is no feeling that it absorbs water from the inside of the mouth. Softness and moistness in cakes are different parameters. For example, traditional sponge cakes are very soft, though they are perceived as not moist (very dry). On the other hand, some brownies can be perceived as very moist and yet be hard and dense. Moisture migration from crumb to crust and amylopectin retrogradation are identified as the main causes of cake firming and cake drying during storage.

Various solutions have been proposed to retard the negative evolution of the texture of cakes during prolonged storage. Among these are special types of emulsifiers, fats, sugars, gums and hydrocolloids. Enzymes such as alpha-amylases have also been described. Amylases do hydrolyse the starch fraction in cake and reduce amylopectin retrogradation during storage. However too extensive hydrolysis of starch using non-specific or too aggressive amylases can negatively influence the volume and the shape of the cake resulting in e.g. the collapse of the cake and/or the cake having inferior cake texture properties.

WO 2006/032281 describes the anti-staling effect in cake of a maltogenic alpha-amylase active in high sugar concentrations. Also, methods to produce cakes wherein the cake batter comprises a lipolytic enzyme and an anti-staling amylase have been tried. All these enzymes or enzymes combinations have mainly an effect on the softness of the cakes. Attempts to further increase the freshness by adding increased amounts of enzymes lead to cakes having the tendency to become perceived as more chewy or harder. Also for bread products different types of enzymes have been added in order to try to increase the softness of the bread products. However, there is an important difference between bread product recipes and cake product recipes. Bread doughs are typically yeast leavened (and may comprise eggs, sugar and/or fat in low amounts) or chemically leavened (typically not comprising eggs, sugar and/or fat), whereas cake batters comprise eggs, sugar and fat in larger amounts and optionally comprise chemical leavening agents. Due to the differences in recipes and chemical processes between bread doughs and cake batters, effects obtained for bread doughs recipes are usually not valid for cake batter recipes.

Today consumers are looking for cakes with improved and/or prolonged freshness that have simultaneously improved or at least conserved/maintained texture properties (cohesiveness and resilience) in order to resist manipulations like packaging, slicing and decorating. There is therefore a need for new and improved cake recipes.

The present invention solves the problems indicated above by providing cake products having improved and/or prolonged freshness, while still maintaining the quality and organoleptic properties of the cake product, including the texture.

SUMMARY OF THE INVENTION

In a first object of the present invention provides in a method for preparing a cake batter or a cake product prepared from the batter, comprising adding in any order one or more raw starch degrading alpha-amylases, one or more phospholipases, and optionally one or more anti-staling amylases to cake batter ingredients, and preparing the cake batter. Preferably, the moistness of said cake product is improved, the moistness preferably being determined by a panel of cake experts. More preferably, the moistness of the cake product is improved by at least 0.5 unit when evaluated on a scale of 1 to 9 and compared to a reference having a fixed value.

In a particular embodiment, the raw starch degrading alpha-amylase is an alpha-amylase having a sequence homology of at least 85%, preferably at least 90%, more preferably at least 95% to SEQ ID NO 1.

In a particular embodiment, the phospholipase is a phospholipase having a sequence homology of at least 85%, preferably at least 90%, more preferably at least 95% to SEQ ID NO 2.

In a particular embodiment, the anti-staling amylase retains more than 20% of its activity in the presence of 10% sucrose.

The present invention further provides in a method according to the invention wherein the cake batter or cake product is chemically leavened. More particularly, said cake batter comprises:

- 15-30% by weight of flour and/or starch, such as untreated flour, heat treated flour, chlorinated flour, modified starch and/or native starch;
- 15-30% by weight of sugar;
- 10-25% by weight of eggs, such as whole eggs, egg white and/or egg yolk;

0-2% by weight of emulsifier, such as mono and diglycerides of fatty acids, propylene glycol esters of fatty acids, lactic acid esters of mono and diglycerides of fatty acids, and/or sodium stearoyl-2-lactylate;

0.3-1% by weight of baking powder, such as containing soda and acid or acidic salts;

0-1% by weight of hydrocolloids, such as Locust bean gum, guar gum, tara gum, xanthan gum, carrageenan, acacia gum, cellulose, modified cellulose, and/or pectin;

10-25% by weight of butter or vegetable fat such as e.g. oil, margarine, shortening, fat paste, or powdered fat; and;

0-15% by weight of water;

with % by weight compared with the total weight of the cake batter.

In a further aspect, the present invention provides in a cake batter or cake product comprising one or more raw starch degrading alpha-amylases, one or more phospholipases, and optionally one or more anti-staling amylases.

In a particular embodiment, the cake batter or cake product according to the invention comprises a raw starch degrading alpha-amylase is an alpha-amylase having a sequence homology of at least 85%, preferably at least 90%, more preferably at least 95% to SEQ ID NO 1 (see Table A).

In a particular embodiment, the cake batter or cake product according to the invention comprises a phospholipase is a phospholipase having a sequence homology of at least 85%, preferably at least 90%, more preferably at least 95% to SEQ ID NO 2 (see Table B).

In a particular embodiment, the cake batter or cake product according to the invention comprises an anti-staling amylase retains more than 20% of its activity in the presence of 10% sucrose.

More particularly, the cake batter according to the invention is a cream cake batter.

More particularly, the cake product according to the invention is a cream cake product.

In a further aspect, the present invention provides in the use of one or more raw starch degrading alpha-amylases, one or more phospholipases, and optionally one or more anti-staling amylases for improving moistness, wherein the moistness is preferably determined by a panel of cake experts.

More particularly the use according to the invention provides that the moistness of the cake product is improved by at least 0.5 unit when evaluated on a scale of 1 to 9 and compared to a reference having a fixed value.

These and further aspects and embodiments are described in the following sections and in the claims.

DETAILED DESCRIPTION OF THE INVENTION

Before the present method and products according to the invention are described, it is to be understood that this invention is not limited to particular methods, products, or devices described, as such methods, products, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The inventors have surprisingly found that, by adding a specific combination of enzymes to a cake batter, it was possible to improve some of the texture and sensorial parameters of the cake, particularly the moistness, while having no negative effect on the others parameters.

When adding raw starch degrading (RSD) amylases to a cake recipe at doses high enough to reduce the hardness of the resulting cake product, it has been observed that this compromises the shape of the cake (i.e. collapse of the top surface). A further negative effect is seen on the texture properties such as the cohesiveness of the cake crumb.

It has now been surprisingly observed that combining a raw starch degrading amylase with a phospholipase significantly improves the moistness of the obtained cake products and this without negative influence on the cohesiveness of the cake product, when compared to a cake product containing the phospholipase alone. This effect was further improved when combining the RSD amylases and the phospholipases with maltogenic anti-staling amylases.

Therefore it is a first object of the present invention to provide a method for preparing a cake batter or a cake product prepared from the batter, comprising adding in any order one or more raw starch degrading alpha-amylases and one or more phospholipases to cake batter ingredients, and preparing the cake batter. It is to be understood that the order in which the different ingredients, including enzymes, are added is impertinent. As such first a cake batter may be prepared from cake batter ingredients followed by the addition in any order of one or more raw starch degrading alpha-amylases and one or more phospholipases to the cake batter, and mixing cake batter ingredients.

In order to further prepare said cake product, said cake batter is baked in order to obtain a cake product. Therefore the method typically comprises the step of baking the cake batter to a cake product.

In a further embodiment the method according to the present invention provides in a method for preparing a cake batter or a cake product prepared from the batter, comprising adding in any order one or more raw starch degrading alpha-amylases, one or more phospholipases, and one or more anti-staling amylases to cake batter ingredients, and preparing the cake batter. It is to be understood that the order in which the different ingredients, including enzymes, are added is impertinent. As such first a cake batter may be prepared from cake batter ingredients followed by the addition in any order of one or more raw starch degrading alpha-amylases, one or more phospholipases, and one or more anti-staling amylases to the cake batter.

According to a particular embodiment, the method according to the present invention provides in a method for preparing a cake product, wherein the cake product is preferably a chemically leavened cake product obtained from the baking of a cake batter, said cake batter preferably comprising as main ingredients flour, eggs and sugar. In preferred embodiments said cake batter further comprises one or more leavening agents and/or fat.

In particular embodiments the method according to the present invention provides in a non-microbiologically leavened cake product comprising flour, eggs, sugar and optionally one or more leavening agents and/or fat.

As referred to herein, the term "leavening agent" refers to any one of a number of substances used in batters that causes the lightening and the softening of the finished product. Formation of carbon dioxide is induced by chemical agents reacting with moisture, heat, acidity, or other triggers. An alternative or supplement to leavening agents is the mechanical leavening of the batter during which air is incorporated into the batter using mechanical means. The leavening agents as referred to herein are chemical compounds such as baking powder. Baking powder typically comprises a carbon dioxide carrier (typically a salt of bicarbonate) and a leavening acid (typically a low molecular weight organic acid). Generally recognized leavening agents may include monocalcium phosphates ($Ca(H_2PO_4)_2$), sodium aluminum sulfate ($NaAl(SO_4)_2 \cdot 12H_2O$), disodium pyrophosphate ($Na_2H_2P_2O_7$), and sodium aluminum phosphates ($NaH_{14}Al_3(PO_4)_8 \cdot 4H_2O$ and $Na_3H_{15}Al_2(PO_4)_8$). These compounds are combined with sodium bicarbonate to give carbon dioxide in a predictable manner.

Additional ingredients may be chosen from the list of fats, lipids, emulsifiers, (milk) proteins, hydrocolloids, gums, starches (native, chemically or physically modified), cocoa powder, chocolate, coloring agents, flavors, etc. The skilled artisan knows how to combine these ingredients to obtain the desired type of cake product.

A cake batter may comprise for example the following ingredients, typically in the following amounts (in % by weight of the batter):

Flour (for example untreated, heat treated, chlorinated, wind sifted, . . . and combinations thereof) and/or starch (modified/native) in an amount between 15 and 30%;

Sugar in an amount between 15 and 30%;

Eggs (whole eggs and/or egg white and/or egg yolk) in an amount between 10 and 25% (calculated as unshelled whole eggs);

Emulsifier (e.g. mono and diglycerides of fatty acids, propylene glycol esters of fatty acids, lactic acid esters of mono and diglycerides of fatty acids, sodium stearoyl-2-lactylate) in an amount between 0 and 2%;

Baking powder (comprising sodium bicarbonate and acid or acidic salts) in an amount between 0.3 and 1%

Hydrocolloids (e.g. locust bean gum, guar gum, tara gum, xanthan gum, carrageenan, acacia gum, cellulose, modified cellulose, pectin) in an amount between 0 and 1%;

Vegetable fat (e.g. oil, margarine, shortening, fat paste, powdered fat) or butter in an amount between 10 and 25%; and;

Water in an amount between 0 and 15%.

In a particular embodiment said cake batter is a cream cake batter comprising for example the following ingredients, typically in the following amounts (in % by weight of the batter):

Flour (untreated, heat treated, chlorinated) in an amount between 20 and 30%;

Sugar in an amount between 20 and 30%;

Eggs (whole eggs and/or egg white and/or egg yolk) in an amount between 15 and 20% (calculated as whole eggs);

Starch (modified, native) in an amount between 0 and 10%;

Emulsifier (e.g. mono and diglycerides of fatty acids, propylene glycol esters of fatty acids, lactic acid esters of mono and diglycerides of fatty acids, sodium stearoyl-2-lactylate) in an amount between 0.5 and 1%;

Baking powder (comprising sodium bicarbonate and acid or acidic salts) in an amount between 0.5 and 1%;

Hydrocolloids (e.g. locust bean gum, guar gum, tara gum, xanthan gum, carrageenan, acacia gum, cellulose, modified cellulose, pectin) in an amount between 0 and 0.5%;

Vegetable fat (e.g. oil) in an amount between 15 and 20%; and;

Water in an amount between 10 and 15%.

According to the present invention the term "raw starch degrading alpha-amylase" or "RSD alpha-amylase", also known as a "raw starch hydrolyzing alpha-amylase" or a "granule starch hydrolyzing alpha-amylase", refers to an enzyme (or in some cases to a combination of enzymes) that can directly degrade raw starch granules at a temperature below the gelatinization temperature of starch, a property that "classical" alpha-amylases do not have. The gelatinization temperature of starch depends on the source of the starch (for example wheat, corn, barley, rye, or rice starch). The gelatinization temperature of starch can range from 51° C. to 78° C. as the gelatinization initiation temperature can vary from about 51° C. to 68° C. A raw starch degrading alpha-amylase is an enzyme that can directly degrade raw starch granules under the following conditions:

When wheat flour is used to make the dough, the raw starch degrading alpha-amylase can directly degrade raw starch when the gelatinization temperature is 52° C. to 75° C.

When corn flour is used to make the dough, the raw starch degrading alpha-amylase can directly degrade raw starch when the gelatinization temperature is 62° C. to 74° C.

When rye flour is used to make the dough, the raw starch degrading alpha-amylase can directly degrade raw starch when the gelatinization temperature is 55° C. to 70° C.

When barley flour is used to make the dough, the raw starch degrading alpha-amylase can directly degrade raw starch when the gelatinization temperature is 53° C. to 63° C.

When oat flour is used to make the dough, the raw starch degrading alpha-amylase can directly degrade raw starch when the gelatinization temperature is 55° C. to 62° C.

When rice flour is used to make the dough, the raw starch degrading alpha-amylase can directly degrade raw starch when the gelatinization temperature is 65° C. to 75° C.

When sorghum flour is used to make the dough, the raw starch degrading alpha-amylase can directly degrade raw starch when the gelatinization temperature is 70° C. to 78° C.

When potato starch is used to make the dough, the raw starch degrading alpha-amylase can directly degrade raw starch when the gelatinization temperature is 56° C. to 69° C.

In a particular embodiment, the raw starch degrading alpha-amylase is defined as an enzyme that has a raw starch degrading index of at least 0.2, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, at least 2, wherein the raw degrading index is a ratio of activity to degrade raw starch to activity to degrade gelatinized starch (Ra/Ga). Preferably, the raw starch degrading alpha-amylase is defined as an enzyme that has a raw starch degrading index of higher than 1. The activity on gelatinized starch is measured by measuring the release of glucose produced by the enzyme on a 2% gelatinized (e.g., corn) starch reaction mixture. The activity is measured by the release of reducing sugars produced in 4 mol per hour per mg of pure active enzyme. The same assay can then be used to measure the activity of the enzyme on raw starch, but substituting the 2% gelatinized (e.g., corn) starch by 2% of raw (e.g., corn) starch. In both assays, the temperature is 40° C., the same pH and buffer solution is used and the incubation time is 6 hours.

In particular embodiments the raw starch degrading alpha-amylases are ubiquitous and produced by plants, animals, and microorganisms, such as, fungal, bacterial and yeast raw starch degrading alpha-amylases. In particular embodiments the raw starch degrading alpha-amylases as used in the present invention may be obtained by genetic modification of known enzymes.

In particular embodiments the raw starch degrading alpha-amylase may preferably be an alpha-amylase comprising a starch-binding domain (SBD) and an alpha-amylase catalytic domain (CD). Examples of such alpha-amylases include the ones disclosed in WO 2005/003311 (which is hereby incorporated by reference), US 2005/0054071 (which is hereby incorporated by reference), U.S. Pat. No. 7,326,548 (which is hereby incorporated by reference), WO 2010/124206 (which is hereby incorporated by reference) and WO 2011/154529 (which is hereby incorporated by reference). Examples also include those enzymes disclosed in Table 1 to 5 of the examples in U.S. Pat. No. 7,326,548, in Table 3 on page 15 of US 2005/0054071, as well as the enzymes disclosed in WO 2004/020499 and WO 2006/06929 and the enzymes disclosed in WO 2006/066579 as SEQ ID NO:2, SEQ ID NO:3, or SEQ ID NO:4. A preferred raw starch degrading acid alpha-amylase enzyme is the hybrid alpha-amylase consisting of *Rhizomucor pusillus* alpha-amylase with *Aspergillus niger* glucoamylase linker and SBD disclosed as V039 in Table 5 in WO 2006/069290.

In a particular embodiment the raw starch degrading alpha-amylase may be a suitable commercial raw-starch degrading alpha-amylases such as SP288 (Novozymes A/S).

More particular the raw-starch degrading alpha-amylase is an alpha-amylase having a sequence identity of at least 85%, preferably at least 90%, more preferably at least 95% to SEQ ID NO 1 (see Table A). In a particular embodiment the raw-starch degrading alpha-amylase is the alpha-amylase with SEQ ID NO 1.

The raw-starch degrading alpha-amylase may be added in an amount of 0.6 to 8.0 FAU-F units per kg of batter, preferably in an amount of 2 to 6 FAU-F per kg of batter, more preferably in an amount of 3.5 to 5.

A suitable method to test the activity of the raw-starch degrading alpha-amylase is the use of a kit containing the substrate (4,6-ethylidene(G7)-p-nitrophenyl(G1)-α,D-maltoheptaoside (ethylidene-G7PNP) and the enzyme α-glucosidase. The presence of an alpha-amylase in a sample converts the substrate to glucose and the yellow-coloured p-nitrophenol that can be detected and measured spectrophotometrically at 405 nm. The reaction conditions are 37° C., pH 7.15 and substrate concentration 1.86 mM. Alpha-amylase activity is expressed in FAU(F) Fungal alpha-Amylase Units and measured relative to an enzyme standard of known strength. An example of enzyme standard is Fungamyl 4000 BG (Novozymes A/S) that contains 4000 FAU(F)/g product.

TABLE A

| Name | Sequence |
| --- | --- |
| SEQ ID NO 1 | ATSDDWKGKAIYQLLTDRFGRADDSTSNCSNLSNYCGGTY EGITKHLDYISGMGFDAIWISPIPKNSDGGYHGYWATDFY QLNSNFGDESQLKALIQAAHERDMYVMLDVVANHAGPTSN GYSGYTFDDASLYHPKCTIDYNNQTSIEQCWVADELPDID TENSDNVAILNDIVSGWVGNYSFDGIRIDTVKHIRKDFWT GYAEAAGVFATGEVFNGDPAYVGPYQKYLPSLINYPMYYA LNDVFVSKSKGFSRISEMLGSNRNAFEDTSVLTTFVDNHD NPRFLNSQSDKALFKNALTYVLLGEGIPIVYYGSEQGFSG GADPANREVLWTTNYDTSSDLYQFIKTVNSVRMKSNKAVY |

TABLE A-continued

| Name | Sequence |
|---|---|
|  | MDIYVGDNAYAFKHGDALVVLNNYGSGSTNQVSFSVSGKF<br>DSGASLMDIVSNITTTVSSDGTVTFNLKDGLPAIFTSATG<br>GTTTTATPTGSGSVTSTSKTTATASKTSTSTSSTSCTTPT<br>AVAVTFDLTATTTYGENIYLVGSISQLGDWETSDGIALSA<br>DKYTSSDPLWYVTVTLPAGESFEYKFIRIESDDSVEWESD<br>PNREYTVPQACGTSTATVTDTWR |

As used herein, the term "sequence identity" or "sequence homology" denotes at least primary structure similarity between two macromolecules, particularly between two polypeptides or polynucleotides, from same or different taxons, wherein said similarity is due to shared ancestry. Preferably, homologous polypeptides will also display similarity in secondary or tertiary structure. Hence, the term 'homologues' denotes so-related macromolecules having said primary and optionally, for proteinaceous macromolecules, secondary or tertiary structure similarity. For comparing two or more polypeptide sequences, the '(percentage of) sequence identity' between a first polypeptide sequence and a second polypeptide sequence may be calculated using methods known by the person skilled in the art, e.g. by dividing the number of polypeptides in the first polypeptide sequence that are identical to the polypeptides at the corresponding positions in the second polypeptide sequence by the total number of polypeptides in the first polypeptide sequence and multiplying by 100% or by using a known computer algorithm for sequence alignment such as NCBI Blast. In determining the degree of sequence identity between two polypeptide, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Two or more polypeptides are said to be 'exactly the same' if they have 100% sequence identity over their entire length.

According to the present invention the term "phospholipase" refers to an enzyme (or in some cases to a combination of enzymes) that catalyzes the release of fatty acyl groups from a phospholipid. In particular embodiments said phospholipase is a phospholipase A2 (PLA2, EC 3.1.1.4) or a phospholipase A1 (EC 3.1.1.32). In further particular embodiments said phospholipase may or may not have other activities such as triacylglycerol lipase (EC 3.1.1.3) and/or galactolipase (EC 3.1.1.26).

In particular embodiments the phospholipase may be a native enzyme derived from mammalian or microbial sources. A particular example of a mammalian phospholipase is pancreatic PLA2, e.g. bovine or porcine PLA2 such as the commercial product Lecitase® 10L (porcine PLA2, product of Novozymes A/S).

In particular embodiments, the microbial phospholipases may be derived from *Fusarium*, e.g. *F. oxysporum* phospholipase A1 (WO 1998/026057 which is hereby incorporated by reference), *F. venenatum* phospholipase A2 (a phospholipase A2 called FvPLA2 described in WO 2004/097012 which is hereby incorporated by reference), from Tuber, e.g. *T. borchii* phospholipase A2 (referred to as TbPLA2 in WO 2004/097012 which is hereby incorporated by reference).

In particular embodiments the microbial phospholipases are commercially available as Lipopan F BG or Lipopan Xtra (Novozymes A/S).

In particular embodiments the phospholipase may also be a lipolytic enzyme variant with phospholipase activity, e.g. as described in WO2000/032758 or WO 2003/060112 (both of which are hereby incorporated by reference).

In particular embodiments the phospholipase may also catalyse the release of fatty acyl groups from other lipids present in the batter, particularly wheat lipids. Thus, the phospholipase may have triacylglycerol lipase activity (EC 3.1.1.3) and/or galactolipase activity (EC 3.1.1.26).

More particular the phospholipase is a lipase having a sequence identity of at least 85%, preferably at least 90%, more preferably at least 95% to SEQ ID NO 2 (see Table B). In a particular embodiment the phospholipase is the phospholipase with SEQ ID NO 2.

In particular embodiments, the phospholipase may be added in an amount of 100-3000 LU units per kg of batter, preferably in an amount of 150 to 2000 LU units per kg of batter, more preferably in an amount of 200 to 800 LU units per kg of batter.

The lipase activity may be determined using tributyrine as substrate. This method is based on the hydrolysis of tributyrin by the enzyme, and the alkali consumption to keep pH constant during hydrolysis is registered as a function of time. One Lipase Unit (LU) is defined as the amount of enzyme which, under standard conditions (i.e. at 30° C.; pH 7.0; with 0.1% w/v Gum Arabic as emulsifier and 0.16 M tributyrine as substrate) liberates 1 µmol titratable butyric acid per minute. A skilled person will understand that other methods may be used to determine the phospholipase activity, for example using lecithin as substrate. In this case, lecithin is hydrolyzed under constant pH and temperature, and the phospholipase activity is determined as the rate of titrant (0.1N NaOH) consumption during neutralization of the liberated fatty acid.

TABLE B

| Name | Sequence |
|---|---|
| SEQ ID<br>NO 2 | MLLLPLLSAITLAVASPVALDDYVNSLEERAVGVTTTD<br>FGNFKFYIQHGAAAYCNSEAAAGSKITCSNNGCPTVQG<br>NGATIVTSFGSKTGIGGYVATDSARKEIVVSFRGSINI<br>RNWLTNLDFGQEDCSLVSGCGVHSGFQRAWNEISSQAT<br>AAVASARKANPSFKVISTGHSLGGAVAVLAAANLRVGG<br>TPVDIYTYGSPRVGNVQLSAFVSNQAGGEYRVTHADDP<br>VPRLPPLIFGYRHTTPEFWLSGGGGDTVDYTISDVKVC<br>EGAANLGCNGGTLGLDIAAHLHYFQATDACNAGGFSWR<br>RYRSAESVDKRATMTDAELEKKLNSYVQMDKEYVKNNQ<br>ARS |

According to the present invention the term "anti-staling amylase", refers to an enzyme capable of retarding crumb firming of the cake when used in effective amount in the cake batter ingredients. Preferably the anti-staling amylase is an anti-staling alpha-amylase. According to a particular embodiment of the present invention the anti-staling alpha-amylase is chosen from the group of anti-staling maltogenic alpha-amylase and anti-staling maltotetraose forming alpha-amylase. Anti-staling maltogenic alpha-amylases and anti-staling maltotetraose forming alpha-amylases are capable of reducing the staling of cake by preventing the loss of softness during prolonged periods of storage.

Preferably the anti-staling maltogenic alpha-amylase is an enzyme classified in EC 3.2.1.133. The primary enzymatic activity of the anti-staling maltogenic alpha-amylase is the catalysis of the release of maltose from amylopectin and amylose. The anti-staling maltogenic alpha-amylase may also hydrolyse maltotriose and cyclodextrins.

The anti-staling alpha-amylases as defined herein may be obtained from any suitable source, in particular from any suitable microorganism and may also be obtained by genetic modification of known enzymes.

Preferred anti-staling maltogenic alpha-amylase are those described in WO91/04669, WO99/43793, WO99/43793, WO2006/032281, WO2008/148845 or EP2486799 (which are hereby all incorporated by reference).

In particular embodiments, the anti-staling maltogenic alpha-amylases are tolerant to high sucrose concentrations. In particular embodiments said anti-staling maltogenic alpha-amylases have a specified sugar tolerance. Compared to the activity of the anti-staling maltogenic alpha-amylases in the absence of sucrose, the anti-staling maltogenic alpha-amylases may have more than 20% activity at 10% sucrose, more than 10% activity at 20% sucrose, or more than 4% activity at 40% sucrose. The sugar tolerance may be determined as described in the examples of WO 2006/032281 (which is hereby incorporated by reference).

In particular embodiments the anti-staling maltogenic alpha-amylases are commercially available as Novamyl®, Opticake® 50 BG, Opticake® Fresh from Novozymes A/S.

An anti-staling maltogenic alpha-amylase, preferably an anti-staling maltogenic alpha-amylase tolerant to high sucrose concentrations, may be added for example in an amount of 10 to 60 SDMU/kg of batter, preferably in an amount of 15 to 50 SDMU/kg of batter, more preferably in an amount of 20 to 40 SDMU/kg of batter.

A suitable method to test the activity of the anti-staling maltogenic alpha-amylase is the use of maltotriose as substrate. The maltogenic alpha-amylase catalyses the hydrolysis of (1-4)-alpha-D-glucosidic linkages in maltotriose so as to release maltose and glucose. The hydrolysis reaction is performed at 37° C. in the following solution: maltotriose 10 mg/ml, $CaCl_2.2H_2O$ 4 mM, Brij 35 112.5 mg/l, sodium citrate 50 mM pH5.0. The released glucose is converted to 6 phosphogluconate and NADH using hexokinase and glucose-6-P-dehydrogenase. NADH is measured spectrophotometrically at 340 nm. The quantity of NADH formed is proportional to the glucose formed and the activity of the enzyme present in the sample. The glucose may be advantageously determined by using a kit commercially available that contains all necessary reagents such as the Glucose (HK) Assay Kit from Sigma-Aldrich. Anti-staling maltogenic alpha-amylase activity is expressed in SDMU (Sweet Dough Maltogenic Unit) and measured relative to an enzyme standard of known strength. An example of enzyme standard is Opticake 50 BG (Novozymes A/S) that contains 50 SDMU/g product.

Preferably the anti-staling maltotetraose forming alpha-amylase is an enzyme classified in EC 3.2.1.60. The primary enzymatic activity of the anti-staling maltotetraose forming enzyme is the catalysis of the release of maltotetraose from amylopectin and amylose.

The anti-staling maltotetraose forming alpha-amylases as defined herein may be obtained from any suitable source, in particular from any suitable microorganism and may also be obtained by genetic modification of known enzymes.

In particular embodiments the anti-staling maltotetraose forming alpha-amylases are those described in WO99/50399 (which is hereby incorporated by reference).

In particular embodiments the anti-staling maltotetraose forming alpha-amylase are commercially available as POW-ERSoft® cake Enzyme from DuPont Industrial Biosciences.

In particular embodiments the anti-staling maltotetraose forming alpha-amylase may be added in an amount of 20 to 500 SKB per kg of batter, preferably in an amount of 50 to 400 SKB per kg of batter, more preferably in an amount of 100 to 300 SKB per kg of batter Anti-staling maltotetraose forming alpha-amylase activity may be measured using the Phadebas® Amylase Test (Magle AB, Sweden). The kit protocol is modified to perform the assay at 45° C. in a 100 mM sodium acetate, 20 mM $CaCl_2.2H_2O$, pH 5.5 buffer. The units given by the standard curve of the kit are converted to SKB/units by multiplying the value by 1.43.

Anti-staling maltotetraose forming alpha-amylase activity may also be measured as described in WO99/50399 (which is hereby incorporated by reference). One unit is defined as the amount of enzyme which releases hydrolysis products equivalent to 1 μmol of reducing sugar per min. when incubated at 50° C. in a test tube with 4 ml of 10 mg/ml waxy maize starch in 50 mM MES buffer, 2 mM calcium chloride, pH 6.0.

In a particular embodiment, the method according to the present invention provides in a method for preparing a cake batter or a cake product prepared from the cake batter wherein the cake batter comprises a raw starch degrading alpha-amylase and a phospholipase, said alpha-amylase having a sequence homology of at least 85%, preferably at least 90%, more preferably at least 95% to SEQ ID NO 1, said phospholipase having a sequence homology of at least 85%, preferably at least 90%, more preferably at least 95% to SEQ ID NO 2. In a particular embodiment the raw-starch degrading alpha-amylase is the alpha-amylase with SEQ ID NO 1 and the phospholipase is the phospholipase with SEQ ID NO 2.

In a particular embodiment, the method according to the present invention provides in a method for preparing a cake batter or a cake product prepared from the cake batter wherein the cake batter comprises a raw starch degrading alpha-amylase, a phospholipase and an anti-staling amylase, said alpha-amylase having a sequence homology of at least 85%, preferably at least 90%, more preferably at least 95% to SEQ ID NO 1, said phospholipase having a sequence homology of at least 85%, preferably at least 90%, more preferably at least 95% to SEQ ID NO 2, said anti-staling amylase being an anti-staling maltogenic alpha-amylase or an anti-staling maltotetraose forming alpha-amylase, preferably an anti-staling amylase characterized in that it retains more than 20% of its activity in the presence of 10% sucrose. In a particular embodiment the raw-starch degrading alpha-amylase is the alpha-amylase with SEQ ID NO 1, the phospholipase is the phospholipase with SEQ ID NO 2 and said anti-staling amylase being an anti-staling maltogenic alpha-amylase or an anti-staling maltotetraose forming alpha-amylase, preferably an anti-staling amylase characterized in that it retains more than 20% of its activity in the presence of 10% sucrose.

In the present invention the hardness (as opposite of softness) and the cohesiveness of a cake (particularly of the cake crumb) may be evaluated by the use of a texture analyzer. In this method the texture parameters are calculated from the curve registered when performing a Texture Profile Analysis (TPA) on a cake sample using a texture analyser. Two consecutive deformations of a cylindrical crumb sample (diameter=45 mm) with a cylindrical probe (diameter=100 mm) with a maximum deformation of 50% of the initial height of the product are performed at a deformation speed of 2 mm/s and a waiting time between the two consecutive deformations of 3 s. The force needed to deform the sample is recorded as a function of time.

The hardness is the maximum force needed to apply a fixed deformation of 50% of the initial height of the cake sample. The cohesiveness is calculated as the ratio (expressed in percent) between the surface under the second deformation curve (downwards+upwards) and the ratio under the first deformation curve (downwards+upwards). A value of 100 is set for the respective texture parameters of the cake that is used as reference in a given test. All other values are expressed relative to this reference.

Cake texture parameters may also be evaluated by performing a sensorial analysis using a panel of cake experts. The cake experts are cake consumers that have been trained to describe and score the different cake texture properties that describe cake freshness: softness, moistness and cohesiveness', all individually and independently. The cake experts use a score card with a scale with scores between 1 and 9 for each parameter. For softness a score of 1 indicates an extremely hard cake, difficult to bite, and a score of 9 indicates an extremely soft cake, with very much less force needed to bite the cake crumb. For moistness, a score of 1 indicates an extremely dry cake crumb and a score of 9 indicates an extremely moist cake. For cohesiveness a score of 1 indicates a very crumbly cake and a score of 9 indicates a very cohesive cake that remains in one piece. Panel members receive a reference cake with a fixed score for the freshness parameter(s) that have to be evaluated and are asked to score the test cakes relatively to the reference cake. Sensorial analyses as described above are calibrated and a value difference of 0.5 is considered as significant.

In a particular embodiment the method according to the present invention provides in a cake product having an improved moistness, the moistness preferably being determined by a panel of cake experts. In a particular embodiment the moistness of said cake product is improved by at least 0.5 unit when evaluated on a scale of 1 to 9 and compared to a reference having a fixed value. More particular the moistness of said cake product is improved by at least 1 unit when evaluated on a scale of 1 to 9 and compared to a reference having a fixed value.

For cohesiveness and softness, a good correlation may be found between texture analysis and sensorial analysis results. However, today there is no reliable physical method to evaluate the moistness of cakes in such a way that they correlate with the sensations felt by a cake consumer.

The texture parameters of cakes may be further evaluated by a panel of persons not trained to sensory evaluation. Typically a group of lambda consumers are asked to compare two or more samples of cake and to either indicate which one is the more soft, moist and/or cohesive or either to rank them on a scale from the less hard/moist/cohesive to the more hard/moist/cohesive.

According to a further aspect, the present invention provides in a cake batter or cake product comprising one or more raw starch degrading alpha-amylases, one or more phospholipases, and optionally one or more anti-staling amylases.

More particular, the cake batter or cake product according to the present invention provide in a cake batter or a cake product prepared from said cake batter wherein the cake batter comprises a raw starch degrading alpha-amylase and a phospholipase, said alpha-amylase having a sequence homology of at least 85%, preferably at least 90%, more preferably at least 95% to SEQ ID NO 1, said phospholipase having a sequence homology of at least 85%, preferably at least 90%, more preferably at least 95% to SEQ ID NO 2.

More particular, the cake batter or cake product according to the present invention provide in a cake batter or a cake product prepared from said cake batter wherein the cake batter comprises a raw starch degrading alpha-amylase, a phospholipase and an anti-staling amylase, said alpha-amylase having a sequence homology of at least 85%, preferably at least 90%, more preferably at least 95% to SEQ ID NO 1, said phospholipase having a sequence homology of at least 85%, preferably at least 90%, more preferably at least 95% to SEQ ID NO 2, said anti-staling amylase being an anti-staling maltogenic alpha-amylase or an anti-staling maltotetraose forming alpha-amylase.

In particular embodiments the cake batter or cake product according to the present invention provides in an anti-staling amylase retaining more than 20% of its activity in the presence of 10% sucrose.

In particular embodiments the cake batter or cake product according to the present invention provides a cream cake batter or cream cake product.

The present invention also relates to cake mixes and cake premixes comprising a phospholipase and a raw starch degrading alpha-amylase, preferably in combination with a maltogenic anti-staling alpha-amylase. Typically a cake mix comprises all the ingredients of a cake recipe with the exception of water, fat (oil, butter, margarine) and eggs. Typically a cake premix is a cake mix where all or part of the flour and sugar has been removed.

In a further aspect, the present invention provides in the use of one or more raw starch degrading alpha-amylases, one or more phospholipases, and optionally one or more anti-staling amylases for improving moistness, wherein the moistness is preferably determined by a panel of cake experts. In particular the moistness of the cake product is improved by at least 0.5 unit when evaluated on a scale of 1 to 9 and compared to a reference having a fixed value.

The present invention also relates to the use of cake mixes and cake premixes as described above to prepare cake product and in particular cream cake products.

EXAMPLES

Example 1

Effect of Raw-starch Degrading Alpha-amylase on Cake Texture

Loaf cream cakes were made using a typical cake batter recipe using the ingredients listed in table 1.

TABLE 1

| Ingredients | w % on batter |
| --- | --- |
| Base Satin Cream Cake * (Puratos N.V., Belgium) | 12 |
| Sugar | 24 |
| Native wheat starch (Syral, Belgium) | 4 |
| Flour (Brabomills NV, Belgium) | 13 |
| Pasteurized whole eggs | 19 |
| Rapeseed oil | 16 |
| Water | 12 |

* Contains emulsifiers, gums, gluten, baking powder, starch, whey powder

Increasing doses (see table 2) of a raw-starch degrading alpha-amylase having the amino acids sequence of SEQ ID NO 1 (referred in this and the following examples as to RSDE) are added to separate batters.

All ingredients are weighed into a mixing bowl starting with the liquid ingredients: water, pasteurised eggs and oil.

All ingredients are first manually mixed with a spatula and subsequently mixed with a planetary mixer (Hobart type N50) for 2 minutes at speed 1 and 2 minutes at speed 2. Portions of 300 g of batter are weighed into aluminum baking tin, placed on a baking tray and baked in a deck oven (MIWE Condo) at 180° C. for 45 minutes. After baking, the cakes (in the tins) are cooled on a rack for two hours at room temperature).

Two hours after baking the shape of the cakes is visually checked, the cakes are packed under modified atmosphere and further stored in a conditioned room at 20° C. until further evaluation. Texture properties are measured using a Stable Micro Systems texture analyser (Type TAXT plus) using the TPA method as described above respectively one day and 21 days after baking. The results are presented in table 2.

TABLE 2

Cake properties

| Enzyme (units FAU-F/kg batter) | Cake shape | Cohesiveness Day 1 | Cohesiveness Day 21 | Hardness Day 1 | Hardness Day 21 |
|---|---|---|---|---|---|
| 0 | OK | 100 | 75 | 100 | 160 |
| 0.91 | OK | 91 | 67 | 100 | 162 |
| 1.52 | OK | 94 | 63 | 106 | 152 |
| 3.04 | OK | 90 | 61 | 105 | 168 |
| 4.56 | Collapse | 90 | 60 | 120 | 175 |
| 6.07 | Collapse | 86 | 49 | 130 | 154 |

The raw-starch degrading alpha-amylase has a negative effect on the shape and the cohesiveness of cakes. At dosages where the cakes do not collapse, there is no significant effect on hardness.

Example 2

Moistness and Softness (Hardness) are not the Same Parameter

Cream cake batters were made using a typical cup cake batter recipe using the ingredients listed in table 3. The enzymes used are RSDE (see example 1), Lipopan F (phospholipase—Novozymes A/S—activity 25000 LU/g) and Opticake 50BG (anti-staling maltogenic amylase—Novozymes A/S—activity 50 SDMU/g).

TABLE 3

| Ingredients | REF2 | PM2 | PMR2 |
|---|---|---|---|
| Cream Cake mix* (w % on batter) (Puratos N.V.) | 53 | 53 | 53 |
| Flour (Brabomills NV, Belgium) | 0.2 | 0.06 | 0.05 |
| Pasteurised whole eggs (w % on batter) | 18.6 | 18.5 | 18.5 |
| Rapeseed oil (w % on batter) | 16 | 16 | 16 |
| Water (w % on batter) | 12 | 12 | 12 |
| RSDE (units FAU-F/kg batter) | 0 | 0 | 4.56 |
| Lipopan F (mg/kg batter) | 0 | 12 | 12 |
| Opticake 50BG (mg/kg batter) | 0 | 590 | 590 |

*contains sugar, flour, emulsifiers, baking powder

Cake hardness is measured one day after baking as described in example 1 (table 4). Sensorial analysis is performed one day after baking as described in example 3 (table 5).

TABLE 4

| Cake crumb hardness | 1 day |
|---|---|
| REF2 | 100 |
| PM2 | 82 |
| PMR2 | 81 |

TABLE 5

| | Average moistness score after 1 day |
|---|---|
| PM2 | 6.5 |
| PMR2 | 7.5 |

The moistness of cup cakes prepared with the addition of a raw-starch degrading alpha-amylase together with a phospholipase and an anti-staling maltogenic alpha-amylase is significantly higher than the moistness of cupcakes prepared with the addition of only a phospholipase and an anti-staling maltogenic alpha-amylase. The hardness (softness) of both cake crumbs remains unchanged.

Example 3

Raw-starch Degrading Enzyme and Phospholipase Act Synergistically

Loaf creams cakes were made using the same recipe and process as in example 1. The enzymes used at the dosages indicated in table 6 are RSDE (see example 1) and Lipopan F (phospholipase—Novozymes A/S).

TABLE 6

| Ingredients | REF3 | P3 | R3 | PR3 |
|---|---|---|---|---|
| RSDE (units FAU-F/kg batter) | 0 | 0 | 4.5 | 3 |
| Lipopan F (mg/kg batter) | 0 | 16 | 0 | 16 |

Two hours after baking the shape of the cakes is visually checked, the cakes are packed under modified atmosphere and further stored in a conditioned room at 20° C. until further evaluation. Texture properties are measured using a Stable Micro Systems texture analyser (Type TAXT plus) using the TPA method as described above respectively one day and 28 days after baking. The results are presented in table 7.

A sensorial analysis of the cakes is performed after 4 weeks storage by a panel of 13 qualified judges who are asked to score the moistness of the cakes between score 1 and score 9 compared to the reference cake for which the moistness score is set at 5.

TABLE 7

Cake properties 4 weeks after baking:

| | moistness | Cohesiveness | Hardness |
|---|---|---|---|
| REF3 | 5.0 | 100 | 100 |
| P3 | 6.0 | 114 | 84 |
| R3 | 6.1 | 99 | 84 |
| PR3 | 7.0 | 119 | 56 |

Example 4

Loaf Cream Cakes

Loaf cream cakes were made using a typical cake batter recipe using the ingredients listed in table 8.

TABLE 8

| Ingredients | w % on batter |
|---|---|
| Base Satin Cream Cake* (Puratos N.V., Belgium) | 12 |
| Potassium sorbate | 0.2 |
| Sugar | 24 |
| Flour (Meneba, Belgium) | 17 |
| Pasteurized whole eggs | 18.8 |
| Rapeseed oil | 16 |
| Water | 12 |

*Contains emulsifiers, gums, gluten, baking powder, starch, whey powder

The enzymes used at the dosages indicated in table 9 are RSDE (see example 1), Lipopan F (phospholipase—Novozymes A/S) and Opticake 50BG (anti-staling maltogenic amylase—Novozymes A/S).

TABLE 9

|  | REF4 | PM4 | PMR4 |
|---|---|---|---|
| RSDE (units-FAU-F/kg batter) | 0 | 0 | 4.55 |
| Lipopan F (mg/kg batter) | 0 | 12 | 12 |
| Opticake 50BG (mg/kg batter) | 0 | 590 | 590 |

The texture of the cakes is measured as described in example 1 respectively after one day and one, two, four and five months after baking (table 10).

A sensorial analysis of the cakes is performed by a panel of qualified judges after one, two, four and five months. The judges have been trained on the evaluation of the texture and the moistness of cakes. Each judge receives a plate with two cake samples and is asked to score the samples on a 1-9 scale according to the perceived moistness. The tests are calibrated by setting a fixed value to the reference cake. A score difference of 0.5 point is perceived by the trained judges and is significant (table 11).

TABLE 10

|  |  | 1 day | 1 month | 2 months | 4 months | 5 months |
|---|---|---|---|---|---|---|
| Hardness | REF4 | 100 | 172 | 194 | 225 | 223 |
|  | PM4 | 92 | 141 | 141 | 161 | 184 |
|  | PMR4 | 59 | 101 | 101 | 104 | 115 |
| Cohesiveness | REF4 | 100 | 76 | 73 | 59 | 64 |
|  | PM4 | 98 | 95 | 94 | 86 | 90 |
|  | PMR4 | 96 | 97 | 97 | 86 | 92 |

TABLE 11

| | Average moistness | | | |
|---|---|---|---|---|
|  | 1 month (8 experts) | 2 months (9 experts) | 4 months (10 experts) | 5 months (9 experts) |
| PM4 | 6.0 | 5.0 | 5.0 | 4.0 |
| PMR4 | 7.6 | 6.8 | 6.8 | 6.3 |

After prolonged storage, cakes prepared with the addition of a combination of a raw-starch degrading alpha-amylase, a phospholipase and an anti-staling maltogenic alpha-amylase are less hard, are more cohesive and are perceived as more moist than cakes prepared with the addition of phospholipase and anti-staling maltogenic amylase.

Example 5

Large Scale Evaluation

Loaf cream cakes were prepared as in example 3. The same enzymes were used at the dosages indicated in table 12.

TABLE 12

|  | PM5 | PMR5 |
|---|---|---|
| RSDE (units FAU-F/kg batter) | 0 | 4.55 |
| Lipopan F (mg/kg batter) | 12 | 12 |
| Opticake 50BG (mg/kg batter) | 590 | 590 |

The texture of the cakes is measured as described in example 1 respectively after one day and two months after baking (table 13).

TABLE 13

|  |  | 1 day | 2 months |
|---|---|---|---|
| Hardness | PM5 | 100 | 182 |
|  | PMR5 | 78 | 135 |
| Cohesiveness | PM5 | 100 | 87 |
|  | PMR5 | 101 | 87 |

A sensorial evaluation of cakes after 2 months storage time has been performed by 115 UK consumers. 66% of the respondents have estimated the cakes labelled PM5 as more moist. This value is statistically significant (Friedman test: p-value: <0.0001, alpha-risk: 5%).

Example 6

Cup Cream Cakes

Cake batters are prepared as described in example 4 with the same enzymes at dosages indicated in table 14.

TABLE 14

|  | REF6 | PM6 | PMR6 |
|---|---|---|---|
| RSDE (units FAU-F/kg batter) | 0 | 0 | 4.55 |
| Lipopan F (mg/kg batter) | 0 | 12 | 12 |
| Opticake 50BG (mg/kg batter) | 0 | 590 | 590 |

Portions of 40 g of the cake batters are weighed manually into paper cup cake cups and are baked for 23 minutes in a deck oven (MIWE Condo) at 180° C. After 2 hours cooling at room temperature, the cup cakes are packed under modified atmosphere and are stored at 20° C.

The cup cake texture is measured as described in example 1 one day, one, two, four and five months after baking with adaptation of the preparation of the cup cakes for the measurement: the paper cup is removed and the top surface of the cup cakes is removed using a sponge cake leveller knife resulting in a cup cake sample of 2.5 cm height. The results are presented in table 15.

A sensorial analysis of the cakes is performed by a panel of qualified judges after one, two, four and five months. The judges have been trained on the evaluation of the texture and the moistness of cakes. Each judge receives a plate with two cake samples and is asked to score the samples on a 1-9 scale according to the perceived moistness. The tests are calibrated by setting a fixed value to the reference cake. A score difference of 0.5 point is perceived by the trained judges and is significant. The results are presented in table 16.

TABLE 15

|  |  | 1 day | 1 month | 2 months | 4 months | 5 months |
|---|---|---|---|---|---|---|
| hardness | REF6 | 100 | 135 | 153 | 201 | 253 |
|  | PM6 | 90 | 117 | 115 | 156 | 187 |
|  | PMR6 | 66 | 82 | 88 | 113 | 130 |
| cohesiveness | REF6 | 100 | 75 | 72 | 69 | 70 |
|  | PM6 | 95 | 81 | 78 | 75 | 79 |
|  | PMR6 | 87 | 80 | 77 | 73 | 76 |

TABLE 16

| | Average moistness score after a storage period of | | | |
|---|---|---|---|---|
| | 1 month (8 experts) | 2 months (9 experts) | 4 months (10 experts) | 5 months (9 experts) |
| PM6 | 5.0 | 5.0 | 5.0 | 3.5 |
| PMR6 | 6.4 | 6.3 | 6.2 | 5.7 |

After prolonged storage, cupcakes prepared with the addition of a combination of a raw-starch degrading alpha-amylase, a phospholipase and an anti-staling maltogenic alpha-amylase are less hard and significantly perceived as more moist than cakes prepared with the addition of phospholipase and anti-staling maltogenic amylase.

Example 7

Other Anti-staling Amylase

Cream cakes batters were prepared and processed as in Example 3. The enzymes are used at the dosages indicated in table 17: RSDE (see example 1), lipopan F (phospholipase—Novozymes A/S) and POWERSoft® Cake Enzyme (anti-staling maltotetraose forming amylase—DuPont Industrial Biosciences).

TABLE 17

|  | REF9 | PM9 | PMR9 |
|---|---|---|---|
| RSDE (units FAU-F/kg batter) | 0 | 0 | 4.55 |
| Lipopan F (mg/kg batter) | 0 | 12 | 12 |

TABLE 17-continued

|  | REF9 | PM9 | PMR9 |
|---|---|---|---|
| POWERSoft ® Cake Enzyme (SKB/kg batter) | 0 | 213 | 213 |

Cake texture is measured one and 21 days after baking as described in Example 1 (table 18). Sensorial analysis is performed one and 21 days after baking as described in Example 3 (table 19)

TABLE 18

|  |  | 1 day | 21 days |
|---|---|---|---|
| Cake crumb hardness | REF7 | 100 | 167 |
|  | PM7 | 73 | 109 |
|  | PMR7 | 56 | 82 |

TABLE 19

|  | Average moistness score after | |
|---|---|---|
|  | 1 day | 21 days |
| PM7 | 7 | 5.5 |
| PMR7 | 8.25 | 7 |

After 21 days of storage, cakes prepared with the addition of a combination of a raw-starch degrading alpha-amylase, a phospholipase and an anti-staling maltotetraose forming alpha-amylase are less hard and perceived as more moist than cakes prepared with the addition of phospholipase and anti-staling maltotetraose forming alpha-amylase.

The invention claimed is:

1. A method for improving the moistness of a cake product, comprising adding in any order one or more raw starch degrading alpha-amylases, one or more phospholipases, and optionally one or more anti-staling amylases to cake batter ingredients, and preparing the cake product, wherein the one or more raw-starch degrading alpha-amylases are added in an amount of 2 to 6 FAU-F units per kg of batter and the one or more phospholipases are added in an amount of 100-3000 LU units per kg of batter, and wherein the moistness of the cake product prepared from the batter comprising the one or more raw starch degrading alpha-amylases, the one or more phospholipases, and optionally one or more anti-staling amylases is improved compared to a cake product prepared from a batter not comprising these enzymes or comprising the phospholipase alone.

2. The method according to claim 1, wherein the moistness of said cake product is determined by a panel of cake experts.

3. The method according to claim 1, wherein the moistness of the cake product is improved by at least 0.5 unit when evaluated on a scale of 1 to 9 and compared to a reference having a fixed value.

4. The method according to claim 1, wherein the raw starch degrading alpha-amylase is an alpha-amylase having a sequence homology of at least 95% to SEQ ID NO 1.

5. The method according to claim 1, wherein the phospholipase is a phospholipase having a sequence homology of at least 95% to SEQ ID NO 2.

6. The method according to claim 1, wherein the anti-staling amylase retains more than 20% of its activity in the presence of 10% sucrose.

7. The method according to claim 1, wherein said cake batter or cake product is chemically leavened.

8. The method according to claim 1, wherein said cake batter comprises:
   15-30% by weight of flour and/or starch;
   15-30% by weight of sugar;
   10-25% by weight of eggs;
   0-2% by weight of emulsifier;
   0.3-1% by weight of baking powder;
   0-1% by weight of hydrocolloids;
   10-25% by weight of butter or vegetable fat; and;
   0-15% by weight of water;
   with % by weight compared with the total weight of the cake batter.

9. A cake batter or cake product comprising one or more raw starch degrading alpha-amylases in an amount of 2 to 6 FAU-F units per kg of batter, one or more phospholipases in an amount of 100-3,000 LU units per kg of batter, and optionally one or more anti-staling amylases, wherein the moistness of the cake product comprising the one or more raw starch degrading alpha-amylases, the one or more phospholipases, and optionally one or more anti-staling amylases is improved compared to a cake product not comprising these enzymes or comprising the phospholipase alone.

10. The cake batter or cake product according to claim 9, wherein the raw starch degrading alpha-amylase is an alpha-amylase having a sequence homology of at least 95% to SEQ ID NO 1.

11. The cake batter or cake product according to claim 9, wherein the phospholipase is a phospholipase having a sequence homology of at least 95% to SEQ ID NO 2.

12. The cake batter or cake product according to claim 10, wherein the anti-staling amylase retains more than 20% of its activity in the presence of 10% sucrose.

13. The cake batter or cake product according to claim 10, wherein said cake batter is a cream cake batter or said cake product is a cream cake product.

14. The cake product according to claim 9, wherein the moistness of the cake product is improved by at least 0.5 unit when evaluated on a scale of 1 to 9 and compared to a reference having a fixed value.

15. The method according to claim 1, wherein the flour and/or starch is untreated flour, heat treated flour, chlorinated flour, modified starch and/or native starch.

16. The method according to claim 1, wherein the eggs are whole eggs, egg white and/or egg yolk.

17. The method according to claim 1, wherein the emulsifier is a mono and diglyceride of fatty acids, propylene glycol ester of fatty acids, lactic acid ester of mono and diglycerides of fatty acids, and/or sodium stearoyl-2-lactylate.

18. The method according to claim 1, wherein the baking powder is a baking powder containing soda and acid or acidic salts.

19. The method according to claim 1, wherein the hydrocolloids are Locust bean gum, guar gum, tara gum, xanthan gum, carrageenan, acacia gum, cellulose, modified cellulose, and/or pectin.

20. The method according to claim 1, wherein the butter or vegetable fat is oil, margarine, shortening, fat paste, or powdered fat.

21. The cake product according to claim 9, wherein the moistness is determined by a panel of cake experts.

* * * * *

SEQUENCE LISTING

<160> NUMBER OF SEQ ID NOS: 2

<210> SEQ ID NO 1

<211> LENGTH: 583
<212> TYPE: PRT
<213> ORGANISM: Artificial sequence
<220> FEATURE:
<223> OTHER INFORMATION: alpha-amylase

<400> SEQUENCE: 1

```
Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Asp
        115                 120                 125

Asp Ala Ser Leu Tyr His Pro Lys Cys Thr Ile Asp Tyr Asn Asn Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
370                 375                 380
```

```
Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
        420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
        450                 455                 460

Ser Lys Thr Ser Thr Thr Ser Ser Thr Ser Cys Thr Thr Pro Thr
465                 470                 475                 480

Ala Val Ala Val Thr Phe Asp Leu Thr Ala Thr Thr Tyr Gly Glu
            485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
        530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
            565                 570                 575

Thr Val Thr Asp Thr Trp Arg
            580

<210> SEQ ID NO 2
<211> LENGTH: 345
<212> TYPE: PRT
<213> ORGANISM: Artificial sequence
<220> FEATURE:
<223> OTHER INFORMATION: phospholipase

<400> SEQUENCE: 2

Met Leu Leu Pro Leu Leu Ser Ala Ile Thr Leu Ala Val Ala Ser
1               5                   10                  15

Pro Val Ala Leu Asp Asp Tyr Val Asn Ser Leu Glu Glu Arg Ala Val
            20                  25                  30

Gly Val Thr Thr Thr Asp Phe Gly Asn Phe Lys Phe Tyr Ile Gln His
            35                  40                  45

Gly Ala Ala Ala Tyr Cys Asn Ser Glu Ala Ala Gly Ser Lys Ile
        50                  55                  60

Thr Cys Ser Asn Asn Gly Cys Pro Thr Val Gln Gly Asn Gly Ala Thr
65                  70                  75                  80

Ile Val Thr Ser Phe Gly Ser Lys Thr Gly Ile Gly Gly Tyr Val Ala
            85                  90                  95

Thr Asp Ser Ala Arg Lys Glu Ile Val Val Ser Phe Arg Gly Ser Ile
            100                 105                 110

Asn Ile Arg Asn Trp Leu Thr Asn Leu Asp Phe Gly Gln Glu Asp Cys
        115                 120                 125

Ser Leu Val Ser Gly Cys Gly Val His Ser Gly Phe Gln Arg Ala Trp
    130                 135                 140

Asn Glu Ile Ser Ser Gln Ala Thr Ala Ala Val Ala Ser Ala Arg Lys
145                 150                 155                 160
```

```
Ala Asn Pro Ser Phe Lys Val Ile Ser Thr Gly His Ser Leu Gly Gly
            165                 170                 175

Ala Val Ala Val Leu Ala Ala Ala Asn Leu Arg Val Gly Gly Thr Pro
            180                 185                 190

Val Asp Ile Tyr Thr Tyr Gly Ser Pro Arg Val Gly Asn Val Gln Leu
            195                 200                 205

Ser Ala Phe Val Ser Asn Gln Ala Gly Gly Glu Tyr Arg Val Thr His
            210                 215                 220

Ala Asp Asp Pro Val Pro Arg Leu Pro Pro Leu Ile Phe Gly Tyr Arg
225                 230                 235                 240

His Thr Thr Pro Glu Phe Trp Leu Ser Gly Gly Gly Gly Asp Thr Val
            245                 250                 255

Asp Tyr Thr Ile Ser Asp Val Lys Val Cys Glu Gly Ala Ala Asn Leu
            260                 265                 270

Gly Cys Asn Gly Gly Thr Leu Gly Leu Asp Ile Ala Ala His Leu His
            275                 280                 285

Tyr Phe Gln Ala Thr Asp Ala Cys Asn Ala Gly Gly Phe Ser Trp Arg
        290                 295                 300

Arg Tyr Arg Ser Ala Glu Ser Val Asp Lys Arg Ala Thr Met Thr Asp
305                 310                 315                 320

Ala Glu Leu Glu Lys Lys Leu Asn Ser Tyr Val Gln Met Asp Lys Glu
            325                 330                 335

Tyr Val Lys Asn Asn Gln Ala Arg Ser
            340                 345
```